US008058230B2

(12) United States Patent

Barbut et al.

(10) Patent No.: US 8,058,230 B2

(45) Date of Patent: Nov. 15, 2011

(54) NEUROTENSIN RECEPTOR AGONISTS AND OPIOID RECEPTOR AGONISTS

(75) Inventors: Denise Barbut, New York, NY (US); Elliott Richelson, Ponte Vedra, FL (US)

(73) Assignees: Sarentis Therapeutics, Inc., New York, NY (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/714,476

(22) Filed: Feb. 27, 2010

(65) Prior Publication Data

US 2010/0210560 A1 Aug. 19, 2010

Related U.S. Application Data

(62) Division of application No. 11/709,991, filed on Feb. 23, 2007, now Pat. No. 7,671,025.

(60) Provisional application No. 60/776,248, filed on Feb. 24, 2006, provisional application No. 60/785,233, filed on Mar. 22, 2006.

(51) Int. Cl.
*A61K 38/10* (2006.01)

(52) U.S. Cl. ........................................ 514/1.1; 514/282

(58) Field of Classification Search ........................ None
See application file for complete search history.

(56) References Cited

U.S. PATENT DOCUMENTS

| | | | | |
|---|---|---|---|---|
| 4,254,107 | A | 3/1981 | Veber | |
| 4,299,838 | A | 11/1981 | Durlach | |
| 4,331,646 | A | 5/1982 | Delaage | |
| 4,518,587 | A | 5/1985 | Laruelle | |
| 5,393,740 | A | 2/1995 | Amagaya | |
| 5,578,651 | A | 11/1996 | Lamberts et al. | |
| 5,631,265 | A | 5/1997 | Audia | |
| 6,046,180 | A | 4/2000 | Jackson | |
| 6,214,790 | B1 | 4/2001 | Richelson | |
| 6,765,099 | B2 | 7/2004 | Richelson | |
| 6,921,805 | B2 | 7/2005 | Richelson | |
| 7,098,307 | B2 | 8/2006 | Richelson | |
| 7,671,025 | B2 * | 3/2010 | Barbut et al. | 514/14 |
| 2002/0187958 | A1 | 12/2002 | Horrobin | |
| 2007/0015718 | A1 | 1/2007 | Mitchell | |
| 2008/0167388 | A1 | 7/2008 | Demopulos | |

FOREIGN PATENT DOCUMENTS

| | | |
|---|---|---|
| EP | 0 333 071 A2 | 9/1989 |
| WO | WO 96/03400 | 2/1996 |
| WO | WO 96/39162 | 12/1996 |
| WO | WO 97/48400 | 12/1997 |

OTHER PUBLICATIONS

Al-Rodhan NR et al., "Structure-antinociceptive activity of neurotensin and some novel analogues in the periaqueductal gray region of the brainstem," Brain Res. 557: 227-235 (1991).

Bissette G et al., "Hypothermia and intolerance to cold induced by intracisternal administration of the hypothalamic peptide neurotensin," Nature 262:607-609 (Aug. 12, 1976).

Carraway R and SE Leeman, "The isolation of a new hypotensive peptide, neurotensin, from bovine hypothalami," J. Biol. Chem. 248: 6854-6861 (Oct. 10, 1973).

Clineschmidt BV and JC McGuffin, "Neurotensin administered intracisternally inhibits responsiveness of mice to noxious stimuli," Eur. J. Pharmacol. 46: 395-396 (1977).

Cusack B et al., "Pharamacological and biochemical profiles of unique neurotensin 8-13 analogs exhibiting species selectivity, stereoselectivity, and superagonism," J. Biol. Chem. 270: 18359-18366 (Aug. 4, 1995).

Cusack B et al., "Pharmacological studies on novel neurotensin mimetics: discovery of a pharmacologically unique agent exhibiting concentration-dependent dual effects as antagonist and agonist," Mol. Pharmacol. 44:1036-1040 (1993).

Cusack B et al., "Effects of a novel neurotensin peptide analog given extracranially on CNS behaviors mediated by apomorphine and haloperidol," Brain Research 856:48-54 (2000).

Fauq AH et al., "Synthesis of (2S)-2-amino-3-(1H-4-indolyl) propanoic acid, a novel tryptophan analog for structural modification of bioactive peptides," Tetrahedron: Asymmetry 9:4127-4134 (1998).

Huang W and Hanson GR, "Differential effect of haloperidol on release of neurotensin in extrapyramidal and limbic systems," Eur. J. Pharmacology 332:15-21 (1997).

Jolicoeur FB et al., "Differential neurobehavioral effects of neurotensin and structural analogues," Peptides 2:171-175 (1981).

Kitabgi P et al., "Neurotensin binding to extraneural and neural receptors: comparison with biological activity and structure-activity relationships," Molecular Pharmacology 18:11-19 (1980).

Lambert PD et al., Anatomy and mechanisms of neurotensin-dopamine interactions in the central nervous system, Annals New York Academy of Sci. 757:377-389 (1995).

Li X-M et al., "Neurotensin peptides antagonistically regulate postsynaptic dopamine D2 receptors in rat nucleus accumbens: a receptor binding and microdialysis study," J. Neural. Transm. 102:125-137 (1995).

Morbeck DE et al., "Analysis of hormone-receptor interaction sites using synthetic peptides: Receptor binding regions of the alpha-subunit of human choriogonadotropin," In: Methods: A Companion to Methods in Enzymology 5:191-200, Academic Press Inc., New York (1993).

Radke JM et al., "Atypical antipsychotic drugs selectively increase neurotensin efflux in dopamine terminal regions," Proc. Natl. Acad. Sci. USA 95:11462-11464 (Sep. 15, 1998).

Sarhan S et al., "Comparative antipsychotic profiles of neurotensin and a related systemically active peptide agonist," Peptides 18(8):1223-1227 (1997).

(Continued)

*Primary Examiner* — Christopher R. Tate
*Assistant Examiner* — Roy Teller
(74) *Attorney, Agent, or Firm* — O'Melveny & Myers LLP

(57) ABSTRACT

This document provides methods and materials for treating pain. For example, this document provides methods that involve administering a neurotensin receptor (NTR) agonist and an opioid receptor agonist to a mammal (e.g., a human). Compositions containing an NTR agonist in combination with an opioid receptor agonist also are provided.

10 Claims, 2 Drawing Sheets

OTHER PUBLICATIONS

Snijders R et al., "Neurotensin induces catalepsy in mice," Neuropharmacology 21: 465-468 (1982).

Troxler von Franz, "Praparative verwendung von mannich-basen von hydroxy-indolen als alkylierungsmittel," Helvetica Chimica Acta, Volumen 51, Fasciculus 6:1214-1224 (1968).

Tyler BM et al., "In vitro binding and CNS effects of novel neurotensin agonists that cross the blood-brain barrier," Neuropharmacology 38:1027-1034 (1999).

Tyler BM et al., "Evidence for additional neurotensin receptor subtypes: neurotensin analogs that distinguish between neurotensin-mediated hypothermia and antinociception," Brain Research 792:246-252 (1998).

Tyler-McMahon et al., "Neurotensin: peptide for the next millennium," Regulatory Peptides 93:125-136 (2000).

Vincent Jean-Pierre et al., "Neurotensin and neurotensin receptors," TIPS 20:302-309 (1999).

* cited by examiner

```
                    SEQUENCE LISTING


<160> NUMBER OF SEQ ID NOS: 39

<210> SEQ ID NO 1
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: pyroGlu

<400> SEQUENCE: 1

Glu Leu Tyr Glu Asn Lys Pro Arg Arg Pro Tyr Ile Leu
1               5                   10


<210> SEQ ID NO 2
<211> LENGTH: 6
<212> TYPE: PRT
<213> ORGANISM: Homo sapiens

<400> SEQUENCE: 2

Arg Arg Pro Tyr Ile Leu
1               5


<210> SEQ ID NO 3
<211> LENGTH: 6
<212> TYPE: PRT
<213> ORGANISM: Artificial Sequence
<220> FEATURE:
<223> OTHER INFORMATION: Oligopeptide -- completely synthesized sequence
<220> FEATURE:
<221> NAME/KEY: MISC_FEATURE
<222> LOCATION: (1)..(1)
<223> OTHER INFORMATION: N-methyl-Arg
<220> FEATURE:
<221> NAME/KEY: MISC_FEATURE
<222> LOCATION: (4)..(4)
<223> OTHER INFORMATION: L-neo-Trp
<220> FEATURE:
<221> NAME/KEY: MISC_FEATURE
<222> LOCATION: (5)..(5)
<223> OTHER INFORMATION: tert-Leu

<400> SEQUENCE: 3

Arg Lys Pro Trp Leu Leu
1               5


<210> SEQ ID NO 4
<211> LENGTH: 13
<212> TYPE: PRT
<213> ORGANISM: Artificial Sequence
<220> FEATURE:
<223> OTHER INFORMATION: NT -- completely synthesized sequence
<220> FEATURE:
<221> NAME/KEY: MISC_FEATURE
<222> LOCATION: (1)..(1)
<223> OTHER INFORMATION: pyroGlu

<400> SEQUENCE: 4
```

Glu Leu Tyr Glu Asn Lys Pro Arg Arg Pro Tyr Ile Leu
1 5 10

<210> SEQ ID NO 5
<211> LENGTH: 6
<212> TYPE: PRT
<213> ORGANISM: Artificial Sequence
<220> FEATURE:
<223> OTHER INFORMATION: NT(8-13) - completely synthesized sequence

<400> SEQUENCE: 5

Arg Arg Pro Tyr Ile Leu
1 5

<210> SEQ ID NO 6
<211> LENGTH: 5
<212> TYPE: PRT
<213> ORGANISM: Artificial Sequence
<220> FEATURE:
<223> OTHER INFORMATION: NTR (9-13) - completely synthesized sequence

<400> SEQUENCE: 6

Arg Pro Tyr Ile Leu
1 5

<210> SEQ ID NO 7
<211> LENGTH: 6
<212> TYPE: PRT
<213> ORGANISM: Artificial Sequence
<220> FEATURE:
<223> OTHER INFORMATION: NTW - completely synthesized sequence

<400> SEQUENCE: 7

Arg Arg Pro Trp Ile Leu
1 5

<210> SEQ ID NO 8
<211> LENGTH: 6
<212> TYPE: PRT
<213> ORGANISM: Artificial Sequence
<220> FEATURE:
<223> OTHER INFORMATION: NT (tert-Leu) - completely synthesized sequence
<220> FEATURE:
<221> NAME/KEY: MISC_FEATURE
<222> LOCATION: (5)..(5)
<223> OTHER INFORMATION: tert-Leu

<400> SEQUENCE: 8

Arg Arg Pro Tyr Leu Leu
1 5

<210> SEQ ID NO 9
<211> LENGTH: 6
<212> TYPE: PRT
<213> ORGANISM: Artificial Sequence
<220> FEATURE:
<223> OTHER INFORMATION: Eisai Co., Ltd. - completely synthesized sequence
<220> FEATURE:
<221> NAME/KEY: MISC_FEATURE
<222> LOCATION: (1)..(1)
<223> OTHER INFORMATION: N-methyl-Arg
<220> FEATURE:
<221> NAME/KEY: MISC_FEATURE
<222> LOCATION: (5)..(5)
<223> OTHER INFORMATION: tert-Leu
<300> PUBLICATION INFORMATION:
<302> TITLE: Polypeptides, Methods for Their Preparation, Pharmaceutical Compositions Comprising Them and Use
<310> PATENT DOCUMENT NUMBER: European Patent Application No. 89104302.8

(Publication No. 0333071)
<311> PATENT FILING DATE: 1989-03-10
<312> PUBLICATION DATE: 1989-09-20

<400> SEQUENCE: 9

Arg Lys Pro Trp Leu Leu
1               5

<210> SEQ ID NO 10
<211> LENGTH: 6
<212> TYPE: PRT
<213> ORGANISM: Artificial Sequence
<220> FEATURE:
<223> OTHER INFORMATION: NT2 - completely synthesized sequence

<400> SEQUENCE: 10

Lys Arg Pro Tyr Ile Leu
1               5

<210> SEQ ID NO 11
<211> LENGTH: 6
<212> TYPE: PRT
<213> ORGANISM: Artificial Sequence
<220> FEATURE:
<223> OTHER INFORMATION: NT24 “27” - completely synthesized sequence
<220> FEATURE:
<221> NAME/KEY: MISC_FEATURE
<222> LOCATION: (2)..(2)
<223> OTHER INFORMATION: Xaa=D-ornithine

<400> SEQUENCE: 11

Arg Xaa Pro Tyr Ile Leu
1               5

<210> SEQ ID NO 12
<211> LENGTH: 6
<212> TYPE: PRT
<213> ORGANISM: Artificial Sequence
<220> FEATURE:
<223> OTHER INFORMATION: NT34 - completely synethesized sequence
<220> FEATURE:
<221> NAME/KEY: MISC_FEATURE
<222> LOCATION: (4)..(4)
<223> OTHER INFORMATION: Xaa=L-3,1'naphthylalanine

<400> SEQUENCE: 12

Arg Arg Pro Xaa Ile Leu
1               5

<210> SEQ ID NO 13
<211> LENGTH: 6
<212> TYPE: PRT
<213> ORGANISM: Artificial Sequence
<220> FEATURE:
<223> OTHER INFORMATION: NT64D - completely synthesized sequence
<220> FEATURE:
<221> NAME/KEY: MISC_FEATURE
<222> LOCATION: (4)..(4)
<223> OTHER INFORMATION: D-neo-Trp

<400> SEQUENCE: 13

Arg Arg Pro Trp Ile Leu
1               5

<210> SEQ ID NO 14
<211> LENGTH: 6
<212> TYPE: PRT
<213> ORGANISM: Artificial Sequence
<220> FEATURE:
<223> OTHER INFORMATION: NT64L - completely synthesized sequence
<220> FEATURE:
<221> NAME/KEY: MISC_FEATURE
<222> LOCATION: (4)..(4)
<223> OTHER INFORMATION: L-neo-Trp

<400> SEQUENCE: 14

Arg Arg Pro Trp Ile Leu
1               5

<210> SEQ ID NO 15
<211> LENGTH: 6
<212> TYPE: PRT
<213> ORGANISM: Artificial Sequence
<220> FEATURE:
<223> OTHER INFORMATION: NT65L - completely synthesized sequence
<220> FEATURE:
<221> NAME/KEY: MISC_FEATURE
<222> LOCATION: (4)..(4)
<223> OTHER INFORMATION: L-neo-trp
<220> FEATURE:
<221> NAME/KEY: MISC_FEATURE
<222> LOCATION: (5)..(5)
<223> OTHER INFORMATION: tert-Leu

<400> SEQUENCE: 15

Arg Arg Pro Trp Leu Leu
1               5

<210> SEQ ID NO 16
<211> LENGTH: 6
<212> TYPE: PRT
<213> ORGANISM: Artificial Sequence
<220> FEATURE:
<223> OTHER INFORMATION: NT66D - completely synthesized sequence
<220> FEATURE:
<221> NAME/KEY: MISC_FEATURE
<222> LOCATION: (4)..(4)
<223> OTHER INFORMATION: D-neo-Trp
<220> FEATURE:
<221> NAME/KEY: MISC_FEATURE
<222> LOCATION: (5)..(5)
<223> OTHER INFORMATION: tert-Leu

<400> SEQUENCE: 16

Lys Arg Pro Trp Leu Leu
1               5

<210> SEQ ID NO 17
<211> LENGTH: 6
<212> TYPE: PRT
<213> ORGANISM: Artificial Sequence
<220> FEATURE:
<223> OTHER INFORMATION: NT66L - completely synthesized sequence
<220> FEATURE:
<221> NAME/KEY: MISC_FEATURE
<222> LOCATION: (4)..(4)
<223> OTHER INFORMATION: L-neo-Trp
<220> FEATURE:
<221> NAME/KEY: MISC_FEATURE
<222> LOCATION: (5)..(5)
<223> OTHER INFORMATION: tert-Leu

<400> SEQUENCE: 17

Lys Arg Pro Trp Leu Leu
1               5

<210> SEQ ID NO 18
<211> LENGTH: 6
<212> TYPE: PRT
<213> ORGANISM: Artificial Sequence
<220> FEATURE:
<223> OTHER INFORMATION: NT67L - completely synthesized sequence
<220> FEATURE:
<221> NAME/KEY: MISC_FEATURE
<222> LOCATION: (4)..(4)
<223> OTHER INFORMATION: L-neo-Trp

<400> SEQUENCE: 18

Lys Arg Pro Trp Ile Leu
1 5

<210> SEQ ID NO 19
<211> LENGTH: 6
<212> TYPE: PRT
<213> ORGANISM: Artificial Sequence
<220> FEATURE:
<223> OTHER INFORMATION: NT69L - completely synthesized sequence
<220> FEATURE:
<221> NAME/KEY: MISC_FEATURE
<222> LOCATION: (1)..(1)
<223> OTHER INFORMATION: N-methyl-Arg
<220> FEATURE:
<221> NAME/KEY: MISC_FEATURE
<222> LOCATION: (4)..(4)
<223> OTHER INFORMATION: L-neo-Trp
<220> FEATURE:
<221> NAME/KEY: MISC_FEATURE
<222> LOCATION: (5)..(5)
<223> OTHER INFORMATION: tert-Leu

<400> SEQUENCE: 19

Arg Lys Pro Trp Leu Leu
1 5

<210> SEQ ID NO 20
<211> LENGTH: 6
<212> TYPE: PRT
<213> ORGANISM: Artificial Sequence
<220> FEATURE:
<223> OTHER INFORMATION: NT69L' - completely synthesized sequence
<220> FEATURE:
<221> NAME/KEY: MISC_FEATURE
<222> LOCATION: (1)..(1)
<223> OTHER INFORMATION: N-methyl-Arg
<220> FEATURE:
<221> NAME/KEY: MISC_FEATURE
<222> LOCATION: (4)..(4)
<223> OTHER INFORMATION: L-neo-Trp
<220> FEATURE:
<221> NAME/KEY: MISC_FEATURE
<222> LOCATION: (5)..(5)
<223> OTHER INFORMATION: tert-Leu

<400> SEQUENCE: 20

Arg Arg Pro Trp Leu Leu
1 5

<210> SEQ ID NO 21
<211> LENGTH: 6
<212> TYPE: PRT
<213> ORGANISM: Artificial Sequence
<220> FEATURE:
<223> OTHER INFORMATION: NT71 - completely synthesized sequence
<220> FEATURE:
<221> NAME/KEY: MISC_FEATURE
<222> LOCATION: (1)..(1)
<223> OTHER INFORMATION: N-methyl-Arg
<220> FEATURE:
<221> NAME/KEY: MISC_FEATURE
<222> LOCATION: (2)..(2)
<223> OTHER INFORMATION: Xaa=diaminobutyric acid
<220> FEATURE:
<221> NAME/KEY: MISC_FEATURE
<222> LOCATION: (4)..(4)
<223> OTHER INFORMATION: L-neo-Trp
<220> FEATURE:

<221> NAME/KEY: MISC_FEATURE
<222> LOCATION: (5)..(5)
<223> OTHER INFORMATION: tert-Leu

<400> SEQUENCE: 21

Arg Xaa Pro Trp Leu Leu
1               5

<210> SEQ ID NO 22
<211> LENGTH: 5
<212> TYPE: PRT
<213> ORGANISM: Artificial Sequence
<220> FEATURE:
<223> OTHER INFORMATION: NT72 - completely synthesized sequence
<220> FEATURE:
<221> NAME/KEY: MISC_FEATURE
<222> LOCATION: (3)..(3)
<223> OTHER INFORMATION: L-neo-Trp
<220> FEATURE:
<221> NAME/KEY: MISC_FEATURE
<222> LOCATION: (4)..(4)
<223> OTHER INFORMATION: tert-Leu

<400> SEQUENCE: 22

Lys Pro Trp Leu Leu
1               5

<210> SEQ ID NO 23
<211> LENGTH: 5
<212> TYPE: PRT
<213> ORGANISM: Artificial Sequence
<220> FEATURE:
<223> OTHER INFORMATION: NT73 - completely synthesized sequence
<220> FEATURE:
<221> NAME/KEY: MISC_FEATURE
<222> LOCATION: (3)..(3)
<223> OTHER INFORMATION: L-neo-Trp

<400> SEQUENCE: 23

Lys Pro Trp Ile Leu
1               5

<210> SEQ ID NO 24
<211> LENGTH: 5
<212> TYPE: PRT
<213> ORGANISM: Artificial Sequence
<220> FEATURE:
<223> OTHER INFORMATION: NT74 - completely synthesized sequence
<220> FEATURE:
<221> NAME/KEY: MISC_FEATURE
<222> LOCATION: (1)..(1)
<223> OTHER INFORMATION: Xaa=diaminobutyric acid
<220> FEATURE:
<221> NAME/KEY: MISC_FEATURE
<222> LOCATION: (3)..(3)
<223> OTHER INFORMATION: L-neo-Trp
<220> FEATURE:
<221> NAME/KEY: MISC_FEATURE
<222> LOCATION: (4)..(4)
<223> OTHER INFORMATION: tert-Leu

<400> SEQUENCE: 24

Xaa Pro Trp Leu Leu
1               5

<210> SEQ ID NO 25
<211> LENGTH: 5
<212> TYPE: PRT
<213> ORGANISM: Artificial Sequence
<220> FEATURE:
<223> OTHER INFORMATION: NT75 - completely synthesized sequence
<220> FEATURE:

<221> NAME/KEY: MISC_FEATURE
<222> LOCATION: (1)..(1)
<223> OTHER INFORMATION: Xaa=diaminobutyric acid
<220> FEATURE:
<221> NAME/KEY: MISC_FEATURE
<222> LOCATION: (3)..(3)
<223> OTHER INFORMATION: L-neo-Trp

<400> SEQUENCE: 25

Xaa Pro Trp Ile Leu
1 5

<210> SEQ ID NO 26
<211> LENGTH: 6
<212> TYPE: PRT
<213> ORGANISM: Artificial Sequence
<220> FEATURE:
<223> OTHER INFORMATION: NT76 - completely synthesized sequence
<220> FEATURE:
<221> NAME/KEY: MISC_FEATURE
<222> LOCATION: (2)..(2)
<223> OTHER INFORMATION: Xaa=D-ornithine
<220> FEATURE:
<221> NAME/KEY: MISC_FEATURE
<222> LOCATION: (4)..(4)
<223> OTHER INFORMATION: L-neo-Trp

<400> SEQUENCE: 26

Arg Xaa Pro Trp Ile Leu
1 5

<210> SEQ ID NO 27
<211> LENGTH: 6
<212> TYPE: PRT
<213> ORGANISM: Artificial Sequence
<220> FEATURE:
<223> OTHER INFORMATION: NT77 - completely synthesized sequence
<220> FEATURE:
<221> NAME/KEY: MISC_FEATURE
<222> LOCATION: (2)..(2)
<223> OTHER INFORMATION: Xaa=D-ornithine
<220> FEATURE:
<221> NAME/KEY: MISC_FEATURE
<222> LOCATION: (4)..(4)
<223> OTHER INFORMATION: L-neo-Trp
<220> FEATURE:
<221> NAME/KEY: MISC_FEATURE
<222> LOCATION: (5)..(5)
<223> OTHER INFORMATION: tert-Leu

<400> SEQUENCE: 27

Arg Xaa Pro Trp Leu Leu
1 5

<210> SEQ ID NO 28
<211> LENGTH: 6
<212> TYPE: PRT
<213> ORGANISM: Artificial Sequence
<220> FEATURE:
<223> OTHER INFORMATION: NT65D - completely synthesized sequence
<220> FEATURE:
<221> NAME/KEY: MISC_FEATURE
<222> LOCATION: (4)..(4)
<223> OTHER INFORMATION: D-neo-Trp
<220> FEATURE:
<221> NAME/KEY: MISC_FEATURE
<222> LOCATION: (5)..(5)
<223> OTHER INFORMATION: tert-Leu

<400> SEQUENCE: 28

Arg Arg Pro Trp Leu Leu
1 5

<210> SEQ ID NO 29
<211> LENGTH: 6
<212> TYPE: PRT
<213> ORGANISM: Artificial Sequence
<220> FEATURE:
<223> OTHER INFORMATION: NT67D - completely synthesized sequence
<220> FEATURE:
<221> NAME/KEY: MISC_FEATURE
<222> LOCATION: (4)..(4)
<223> OTHER INFORMATION: D-neo-Trp

<400> SEQUENCE: 29

Lys Arg Pro Trp Ile Leu
1               5

<210> SEQ ID NO 30
<211> LENGTH: 6
<212> TYPE: PRT
<213> ORGANISM: Artificial Sequence
<220> FEATURE:
<223> OTHER INFORMATION: NT69D - completely synthesized sequence
<220> FEATURE:
<221> NAME/KEY: MISC_FEATURE
<222> LOCATION: (1)..(1)
<223> OTHER INFORMATION: N-methyl-Arg
<220> FEATURE:
<221> NAME/KEY: MISC_FEATURE
<222> LOCATION: (4)..(4)
<223> OTHER INFORMATION: D-neo-Trp

<400> SEQUENCE: 30

Arg Lys Pro Trp Leu Leu
1               5

<210> SEQ ID NO 31
<211> LENGTH: 6
<212> TYPE: PRT
<213> ORGANISM: Artificial Sequence
<220> FEATURE:
<223> OTHER INFORMATION: NT71D - completely synthesized sequence
<220> FEATURE:
<221> NAME/KEY: MISC_FEATURE
<222> LOCATION: (1)..(1)
<223> OTHER INFORMATION: N-methyl-Arg
<220> FEATURE:
<221> NAME/KEY: MISC_FEATURE
<222> LOCATION: (2)..(2)
<223> OTHER INFORMATION: Xaa=diaminobutyric acid
<220> FEATURE:
<221> NAME/KEY: MISC_FEATURE
<222> LOCATION: (4)..(4)
<223> OTHER INFORMATION: D-neo-Trp
<220> FEATURE:
<221> NAME/KEY: MISC_FEATURE
<222> LOCATION: (5)..(5)
<223> OTHER INFORMATION: tert-Leu

<400> SEQUENCE: 31

Arg Xaa Pro Trp Leu Leu
1               5

<210> SEQ ID NO 32
<211> LENGTH: 5
<212> TYPE: PRT
<213> ORGANISM: Artificial Sequence
<220> FEATURE:
<223> OTHER INFORMATION: NT72D - completely synthesized sequence
<220> FEATURE:
<221> NAME/KEY: MISC_FEATURE
<222> LOCATION: (3)..(3)
<223> OTHER INFORMATION: D-neo-Trp
<220> FEATURE:
<221> NAME/KEY: MISC_FEATURE
<222> LOCATION: (4)..(4)
<223> OTHER INFORMATION: tert-Leu

<400> SEQUENCE: 32

Lys Pro Trp Leu Leu
1 5

<210> SEQ ID NO 33
<211> LENGTH: 5
<212> TYPE: PRT
<213> ORGANISM: Artificial Sequence
<220> FEATURE:
<223> OTHER INFORMATION: NT73D - completely synthesized sequence
<220> FEATURE:
<221> NAME/KEY: MISC_FEATURE
<222> LOCATION: (3)..(3)
<223> OTHER INFORMATION: D-neo-Trp

<400> SEQUENCE: 33

Lys Pro Trp Ile Leu
1 5

<210> SEQ ID NO 34
<211> LENGTH: 5
<212> TYPE: PRT
<213> ORGANISM: Artificial Sequence
<220> FEATURE:
<223> OTHER INFORMATION: NT74D - completely synthesized sequence
<220> FEATURE:
<221> NAME/KEY: MISC_FEATURE
<222> LOCATION: (1)..(1)
<223> OTHER INFORMATION: Xaa=diaminobutyric acid
<220> FEATURE:
<221> NAME/KEY: MISC_FEATURE
<222> LOCATION: (3)..(3)
<223> OTHER INFORMATION: D-neo-Trp
<220> FEATURE:
<221> NAME/KEY: MISC_FEATURE
<222> LOCATION: (4)..(4)
<223> OTHER INFORMATION: tert-Leu

<400> SEQUENCE: 34

Xaa Pro Trp Leu Leu
1 5

<210> SEQ ID NO 35
<211> LENGTH: 5
<212> TYPE: PRT
<213> ORGANISM: Artificial Sequence
<220> FEATURE:
<223> OTHER INFORMATION: NT75D - completely synthesized sequence
<220> FEATURE:
<221> NAME/KEY: MISC_FEATURE
<222> LOCATION: (1)..(1)
<223> OTHER INFORMATION: Xaa=diaminobutyric acid
<220> FEATURE:
<221> NAME/KEY: MISC_FEATURE
<222> LOCATION: (3)..(3)
<223> OTHER INFORMATION: D-neo-Trp

<400> SEQUENCE: 35

Xaa Pro Trp Ile Leu
1 5

<210> SEQ ID NO 36
<211> LENGTH: 6
<212> TYPE: PRT
<213> ORGANISM: Artificial Sequence
<220> FEATURE:
<223> OTHER INFORMATION: NT76D - completely synthesized sequence
<220> FEATURE:
<221> NAME/KEY: MISC_FEATURE
<222> LOCATION: (2)..(2)
<223> OTHER INFORMATION: Xaa=D-ornithine
<220> FEATURE:
<221> NAME/KEY: MISC_FEATURE
<222> LOCATION: (4)..(4)
<223> OTHER INFORMATION: D-neo-Trp

<400> SEQUENCE: 36

Arg Xaa Pro Trp Ile Leu
1 5

<210> SEQ ID NO 37
<211> LENGTH: 6
<212> TYPE: PRT
<213> ORGANISM: Artificial Sequence
<220> FEATURE:
<223> OTHER INFORMATION: NT77D - completely synthesized sequence
<220> FEATURE:
<221> NAME/KEY: MISC_FEATURE
<222> LOCATION: (2)..(2)
<223> OTHER INFORMATION: Xaa=D-ornithine
<220> FEATURE:
<221> NAME/KEY: MISC_FEATURE
<222> LOCATION: (4)..(4)
<223> OTHER INFORMATION: D-neo-Trp
<220> FEATURE:
<221> NAME/KEY: MISC_FEATURE
<222> LOCATION: (5)..(5)
<223> OTHER INFORMATION: tert-Leu

<400> SEQUENCE: 37

Arg Xaa Pro Trp Leu Leu
1 5

<210> SEQ ID NO 38
<211> LENGTH: 6
<212> TYPE: PRT
<213> ORGANISM: Artificial Sequence
<220> FEATURE:
<223> OTHER INFORMATION: NT78L - completely synthesized sequence
<220> FEATURE:
<221> NAME/KEY: MISC_FEATURE
<222> LOCATION: (1)..(1)
<223> OTHER INFORMATION: N-methyl-Arg
<220> FEATURE:
<221> NAME/KEY: MISC_FEATURE
<222> LOCATION: (2)..(2)
<223> OTHER INFORMATION: Xaa=D-Ornithine
<220> FEATURE:
<221> NAME/KEY: MISC_FEATURE
<222> LOCATION: (4)..(4)
<223> OTHER INFORMATION: Xaa=L-neo-Trp
<220> FEATURE:
<221> NAME/KEY: MISC_FEATURE
<222> LOCATION: (5)..(5)
<223> OTHER INFORMATION: tert-Leu

<400> SEQUENCE: 38

Arg Xaa Pro Trp Leu Leu
1 5

<210> SEQ ID NO 39
<211> LENGTH: 6
<212> TYPE: PRT
<213> ORGANISM: Artificial Sequence
<220> FEATURE:
<223> OTHER INFORMATION: NT78D - completely synthesized sequence
<220> FEATURE:
<221> NAME/KEY: MISC_FEATURE
<222> LOCATION: (1)..(1)
<223> OTHER INFORMATION: N-methyl-Arg
<220> FEATURE:
<221> NAME/KEY: MISC_FEATURE
<222> LOCATION: (2)..(2)

-continued

```
<223> OTHER INFORMATION: Xaa=D-Ornithine
<220> FEATURE:
<221> NAME/KEY: MISC_FEATURE
<222> LOCATION: (4)..(4)
<223> OTHER INFORMATION: D-neo-Trp
<220> FEATURE:
<221> NAME/KEY: MISC_FEATURE
<222> LOCATION: (5)..(5)
<223> OTHER INFORMATION: tert-Leu

<400> SEQUENCE: 39

Arg Xaa Pro Trp Leu Leu
1               5
```

NEUROTENSIN RECEPTOR AGONISTS AND OPIOID RECEPTOR AGONISTS

REFERENCE TO RELATED APPLICATIONS

This application is a divisional of U.S. application Ser. No. 11/709,991, filed Feb. 23, 2007, now U.S. Pat. No. 7,671,025 which claims priority to U.S. Provisional Application Ser. No. 60/776,248 filed Feb. 24, 2006, entitled "Neurotensin Receptor Agonists and Opioid Receptor Agonists," and U.S. Provisional Application Ser. No. 60/785,233, filed Mar. 22, 2006, entitled "Synergistic Neurotensin-Opiate Compositions and Methods of Use," all of which are hereby expressly incorporated by reference in their entirety.

BACKGROUND

1. Technical Field

The subject matter herein relates to analgesic compositions, formulations, and methods of use and to synergistic combinations of neurotensins or analogs and opiates or analogs that reduce their side effect profile at the same or increased analgesic potency.

2. Background Information

Analgesics are used in the treatment of pain, the cause of which can vary from acute wounds such as cuts, bruises, surgical incisions, or burns to chronic conditions such as structural defects (e.g., back, joint, or spinal disc problems) or diseases (e.g., cancer, inflammatory conditions, or infections).

Analgesics have an ability to reduce perception of pain impulses by the central nervous system. Opiates are the most widely used analgesics in the treatment of severe pain. Opiates bind a variety of receptors, including mu, delta, and kappa receptors. Both the endogenous opioid peptides and synthetic opiate analgesics alter the central or peripheral release of neurotransmitters from afferent nerves sensitive to noxious stimuli. The specific actions of the narcotic analgesics can be defined by their sensitivity and selectivity for binding at three specific opiate receptor types, mu, kappa, and delta. The mu opiates have high affinity and selectivity for binding sites in the brain and analgesic action is mostly attributed to these receptors. Delta receptors are mostly located in the spinal cord and may have a role in peripheral pain. Kappa receptors are located in the hypothalamus and may account for the neuro-endocrine actions associated with kappa binding.

Narcotic analgesics are also classified as agonists, mixed agonist-antagonists, or partial agonists by their activity at opiate receptors. Narcotic agonists include natural opium alkaloids (e.g., morphine, codeine), semisynthetic analogs (e.g., hydromorphone, oxymorphone, oxycodone), and synthetic compounds (e.g., meperidine, levorphanol, methadone, sufentanil, alfentanil, fentanyl, remifentanil, levomethadyl). Mixed agonist-antagonist drugs (e.g., nalbuphine, pentazocine) have agonist activity at some receptors and antagonist activity at other receptors; partial agonists (e.g., butorphanol, buprenorphine) are also included. Narcotic antagonists (e.g., naloxone) do not have agonist activity at any of the opiate receptor sites. Antagonists block the opiate receptor, inhibit pharmacological activity of the agonist, and precipitate withdrawal in dependent patients.

When given acutely in the treatment of severe pain, e.g., in post-op pain, opiates produce a variety of secondary pharmacological side-effects, ranging from mild to life threatening. Cough and respiration are depressed, and fatal doses lead to severe respiratory depression by direct inhibition of the respiratory center in the brain stem. Nausea and vomiting occur in many individuals through direct stimulation of the chemoreceptor trigger zone. Therapeutic doses also result in inhibition of baroreceptor responses and hypotension, the latter through the release of histamine. Gastrointestinal motility is reduced, resulting in constipation. Sedation occurs and cognitive function is impaired. Extended use of opiates, as in the treatment of cancer pain, is associated with dependence, tolerance, and potential for drug abuse.

Neurotensin and its analogs are also potent analgesic in animals. Like opiates, they are produced in the brain, spinal cord dorsal horn, hypothalamus, and gut. In all these locations, cells producing neurotensin are in close proximity to those producing endogenous opiates, which is consistent with the fact that neurotensin and opiates have similar actions. Several different neurotensin receptors (NTRs, e.g., NTR1, NTR2, and NTR3) have been identified to date, presumably with slightly different functions. Several similarities exist in the actions between neurotensin and opiates. First, neurotensin receptors involved in the treatment of central pain may be different than those involved in the treatment of peripheral pain. Second, neurotensin administration is associated with not just analgesia but hypotension (unrelated to histamine release), fall in basal temperature, and weight loss. Third, neurotensin induces tolerance. However, unlike opiates, neurotensin does not depress respiration, suppress coughing, induce constipation, alter cognitive function or cause sedation. Neurotensin is known to increase gastrointestinal transit and induce diarrhea. Neurotensin has also been shown to exhibit antipsychotic effect and antiparkinsonian effect.

To minimize side effects generated by giving a specific opiate, different opiates can be combined to produce synergistic analgesic effects. Synergism is defined as correlated action of two or more agents so that the combined action is greater than the sum of each acting separately. For example, when morphine and methadone are combined, analgesic synergy is achieved but not accompanied by synergistic effect in other pharmacological actions, such as in gut motility. This synergy between the opiates is useful because unwanted side effects associated with both acute and long-term administration of the opiates can be diminished without reducing analgesic potency. However, synergistic action between different opiates remains unclear because two opiates acting on the same receptors, namely mu receptors, may not exhibit synergy. For example, methadone is only synergistic with morphine, codeine, 6-acetyl morphine, and morphine-6-beta glucuronide but not with fentanyl, oxymorphone, oxycodone, meperidine, or alfentanyl. All of the above mentioned opiates are mu receptor agonists. Similarly, morphine is synergistic only with methadone but none of the other mu agonists.

Opiates remain the drug of choice in management of severe pain to date. However, new agents and methods are needed to provide alternative pain management, with or without opiates. Alternative agents and methods are needed to enhance the pharmacological effect and minimize unwanted side effects of opiates, such as tolerance, dependence, and constipation.

SUMMARY

The subject matter herein provides compositions and methods for treating pain by combining different analgesics to achieve synergy between the analgesic agents and reduce their side effect profile. Although the mechanism of action and receptor binding for different classes of analgesics are different, the results provided herein demonstrate that the use of opiates or opiate receptor agonists in combination with other analgesics, such as neurotensins or neurotensins receptor agonists, can achieve a synergistic analgesic effect and can reduce constipation as well as tolerance and dependence to both opiate and NT. The method by which opiate dependence is diminished or blocked is not just that smaller doses of opiate can be used but also that NT can block the dopaminergic reward system. Furthermore, the hypotension attributable to larger doses of NT can be eliminated.

NTR agonists and opioid receptor agonists are typically administered in amounts effective to reduce the level of pain experienced by the mammal. As disclosed herein, administering an NTR agonist together with an opioid receptor agonist provides a mammal with a greater level of pain relief than when either the NTR agonist or the opioid receptor agonist is used alone. Examples of NTR agonists include, without limitation, neurotensin (NT) polypeptide analogs such as NT69L. Examples of opioid receptor agonists include, without limitation, morphine, codeine, and nalorphine hydrochloride. The subject matter herein also provides compositions containing an NTR agonist in combination with an opioid receptor agonist. For example, a composition can be formulated to contain morphine and NT69L. The compositions provided herein can be used to treat pain.

In one aspect, the subject matter herein features methods for treating pain comprising administering a neurotensin receptor agonist and an opioid receptor agonist to a mammal. The neurotensin receptor agonist can be a polypeptide. The polypeptide can contain an amino acid analog (e.g., L-neo-Trp). The polypeptide can be selected from the group consisting of NT(1-13), NT(8-13), NT69L, NT69L', and NT76. The administering can be by injection. The opioid receptor agonist can be morphine. The method can comprise administering a composition containing the neurotensin receptor agonist and the opioid receptor agonist. The method can comprise administering the neurotensin receptor agonist prior to administering the opioid receptor agonist. The method can comprise administering the opioid receptor agonist prior to administering the neurotensin receptor agonist.

In another aspect, the subject matter herein features a composition containing a neurotensin receptor agonist and an opioid receptor agonist. The neurotensin receptor agonist can be a polypeptide selected from the group consisting of NT(1-13), NT(8-13), NT69L, NT69L', and NT76. The opioid receptor agonist compound can be morphine. The composition can contain a pharmaceutically acceptable carrier. The composition can contain two or more neurotensin receptor agonists. The composition can contain two or more opioid receptor agonists.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
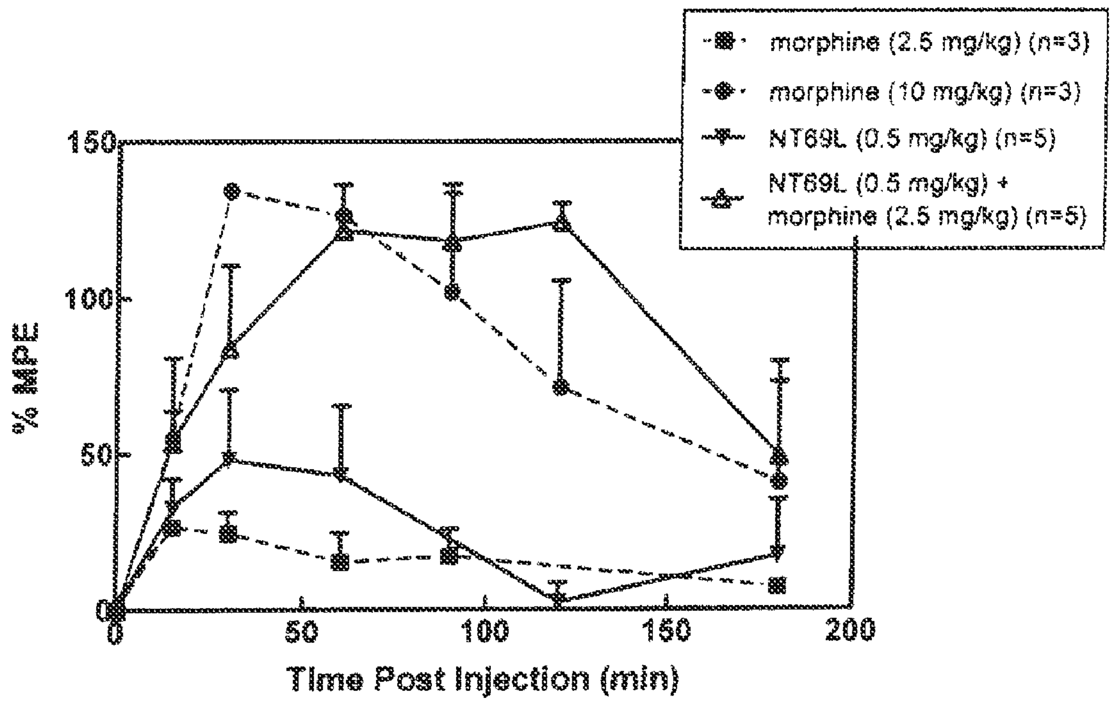
FIG. 1 is a graph plotting the percent maximum possible effect at the indicated time post injection for rats treated with morphine alone (2.5 or 10.0 mg/kg), NT69L alone (0.5 mg/kg), or both morphine (2.5 mg/kg) and NT69L (0.5 mg/kg).

The methods described herein include administering at least one (e.g., one, two, three, four, five, six, or more) NTR agonist and at least one (e.g., one, two, three, four, five, six, or more) opioid receptor agonist to a mammal (e.g., a mouse, rat, dog, cat, horse, cow, pig, monkey, or human). The term "NTR agonist" as used herein refers to any molecule that binds to an NTR and induces an NTR response. NTR agonists include, without limitation, polypeptides and other agents such as small molecules. For example, an NTR agonist can be a polypeptide such as NT, NT(1-13), NT(8-13), and NT69L. Examples of opioid receptor agonists include, without limitation, alfentanil hydrochloride, alphaprodine, anileridine hydrochloride, buprenorphine hydrochloride, butorphanol tartrate, codeine, codeine phosphate, codeine sulfate, fentanyl citrate, heroin, hydrocodone tartrate, hydromorphone hydrochloride, ketobemidone, levorphanol tartrate, meperidine hydrochloride, meptazinol hydrochloride, methyl fentanyl, morphine, morphine acetate, morphine sulfate, nalbuphine hydrochloride, nalorphine hydrochloride, oxycodone hydrochloride, oxymorphone hydrochloride, pholcodine, remifentanil hydrochloride, sufentanil citrate, and tramadol hydrochloride.

Typically, NTR agonists induce NTR responses such as antinociception, hypothermia, diminished food consumption, blockade of muscle rigidity (catalepsy) caused by antipsychotic drugs (e.g., haloperidol), and inhibition of climbing behavior caused by the dopamine receptor agonist apomorphine. NTR responses can be measured using any method. For example, antinociception can be measured using pain tests such as tail flick and paw withdrawal studies. Briefly, tail flick and paw withdrawal studies typically involve subjecting an animal to a painful stimulus (e.g., heat, a pin prick, or a pinch on the foot), and measuring the length of time or amount of pinching force applied before the animal physically responds to the stimulus by flicking its tail or withdrawing its paw. NTR effects also can be measured in any suitable cell system. For example, NTR effects (at NTR1) can be measured in human colonic adenoma cells (HT29 cells) by measuring the formation of second messengers (e.g., release of inositol phosphates or increase in intracellular levels of calcium ions). The specificity of NTR responses can be confirmed using NTR antagonists such as SR48692 and SR142948A.

NT is a tridecapeptide (Carraway and Leeman (1973) *J. Biol. Chem.* 248:6854-6861) that induces antinociception and hypothermia upon direct administration to brain. Systemic administration of NT does not induce these effects, however, since NT is rapidly degraded by proteases and has poor blood brain barrier permeability. NT behaves as a neurotransmitter or neuromodulator in the CNS, and there are striking interactions between NT (via its receptors) and central dopaminergic systems (Tyler-McMahon et al. (2000) *Regul. Pept.* 93:125-136; and Lambert et al. (1995) *Ann. NY Acad. Sci.* 757:377-389).

The complete amino acid sequence of NT(1-13) is pyro-Glu-Leu-Tyr-Glu-Asn-Lys-Pro-Arg-Arg-Pro-Tyr-Ile-Leu (SEQ ID NO:1). Most, if not all, of the activity mediated by NT(1-13) also can be seen with the shorter fragment, NT(8-13), which has the sequence Arg-Arg-Pro-Tyr-Ile-Leu (SEQ ID NO:2). These NT polypeptides, as well as other NTR agonists, can be used as described herein to provide pain relief.

NTR agonists that can be used in combination with an opioid receptor agonist to treat pain include, without limitation, brain-penetrating analogs of NT polypeptides. Such polypeptides can have amino acid sequences that are based on the sequence of NT(8-13) and can incorporate one or more amino acid analogs such as D- or L-neo-tryptophan (Fauq et al. (1998) *Tetrahedron: Assymetry* 9:4127-4134). Neo-tryptophan (2-amino-3-[1H-indolyl]propanoic acid) places the indole group of tryptophan in a unique orientation in terms of steric and electrostatic fields, such that polypeptides containing neo-tryptophan provide novel arrangements for side chain interactions. For example, this document provides methods for using polypeptides having the amino acid sequence N-methyl-Arg-Lys-Pro-L-neo-Trp-tert-Leu-Leu (SEQ ID NO:3; referred to herein as NT69L). Examples of other polypeptides that are NT analogs are provided herein in Table 1.

TABLE I

Amino acid sequences of selected NTR agonists

| Polypeptide | 1 | 2 | 3 | 4 | 5 | 6 | 7 | 8 | 9 | 10 | 11 | 12 | 13 |
|---|---|---|---|---|---|---|---|---|---|---|---|---|---|
| NT SEQ ID NO. NO. 4 | p-Glu | L-Leu | L-Tyr | L-Glu | L-Asn | L-Lys | L-Pro | L-Arg | L-Arg | L-Pro | L-Tyr | L-Ile | L-Leu |
| NT(8-13) SEQ ID NO. 5 | | | | | | | | L-Arg | L-Arg | L-Pro | L-Tyr | L-Ile | L-Leu |
| NT(9-13) SEQ ID NO. 6 | | | | | | | | | L-Arg | L-Pro | L-Tyr | L-Ile | L-Leu |
| NTW SEQ ID NO. 7 | | | | | | | | L-Arg | L-Arg | L-Pro | L-Trp | L-Ile | L-Leu |
| NT (tert-Leu) SEQ ID NO. 8 | | | | | | | | L-Arg | L-Arg | L-Pro | L-Tyr | tert-Leu | L-Leu |
| Eisai* SEQ ID NO. 9 | | | | | | | | N-methyl-Arg | L-Lys | L-Pro | L-Trp | tert-Leu | L-Leu |
| NT2 SEQ ID NO. 10 | | | | | | | | D-Lys | L-Arg | L-Pro | L-Tyr | L-Ile | L-Leu |
| NT24 "27" SEQ ID NO. 11 | | | | | | | | L-Arg | D-Orn[&] | L-Pro | L-Tyr | L-Ile | L-Leu |
| NT34 SEQ ID NO. 12 | | | | | | | | L-Arg | L-Arg | L-Pro | L-3,1'-Nal[#] | L-Ile | L-Leu |
| NT64D SEQ ID NO. 13 | | | | | | | | L-Arg | L-Arg | L-Pro | D-neo-Trp | L-Ile | L-Leu |
| NT64L SEQ ID NO. 14 | | | | | | | | L-Arg | L-Arg | L-Pro | L-neo-Trp | L-Ile | L-Leu |
| NT65L SEQ ID NO. 15 | | | | | | | | L-Arg | L-Arg | L-Pro | L-neo-Trp | tert-Leu | L-Leu |
| NT66D SEQ ID NO. 16 | | | | | | | | D-Lys | L-Arg | L-Pro | D-neo-Trp | tert-Leu | L-Leu |
| NT66L SEQ ID NO. 17 | | | | | | | | D-Lys | L-Arg | L-Pro | L-neo-Trp | tert-Leu | L-Leu |

TABLE I-continued

| Amino acid sequences of selected NTR agonists | | | | | | | | | | | | |
|---|---|---|---|---|---|---|---|---|---|---|---|---|
| Polypeptide 1 | 2 | 3 | 4 | 5 | 6 | 7 | 8 | 9 | 10 | 11 | 12 | 13 |
| NT67L SEQ ID NO. 18 | | | | | | | D-Lys | L-Arg | L-Pro | L-neo-Trp | L-Ile | L-Leu |
| NT69L SEQ ID NO. 19 | | | | | | | N-methyl-Arg | L-Lys | L-Pro | L-neo-Trp | tert-Leu | L-Leu |
| NT69L' SEQ ID NO. 20 | | | | | | | N-methyl-Arg | L-Arg | L-Pro | L-neo-Trp | tert-Leu | L-Leu |
| NT71 SEQ ID NO. 21 | | | | | | | N-methyl-Arg | DAB[$] | L-Pro | L-neo-Trp | tert-Leu | L-Leu |
| NT72 SEQ ID NO. 22 | | | | | | | | D-Lys | L-Pro | L-neo-Trp | tert-Leu | L-Leu |
| NT73 SEQ ID NO. 23 | | | | | | | | D-Lys | L-Pro | L-neo-Trp | L-Ile | L-Leu |
| NT74 SEQ ID NO. 24 | | | | | | | | DAB | L-Pro | L-neo-Trp | tert-Leu | L-Leu |
| NT75 SEQ ID NO. 25 | | | | | | | | DAB | L-Pro | L-neo-Trp | L-Ile | L-Leu |
| NT76 SEQ ID NO. 26 | | | | | | | L-Arg | D-Orn | L-Pro | L-neo-Trp | L-Ile | L-Leu |
| NT77 SEQ ID NO. 27 | | | | | | | L-Arg | D-Orn | L-Pro | L-neo-Trp | tert-Leu | L-Leu |

*Tsuchiya Y et al., (1989) European Patent Application 89104302.8;
[#]naphthylalanine;
[$]diaminobutyric acid;
[&]D-ornithine As used herein, a "polypeptide" is any chain of amino acid residues, regardless of post-translational modification (e.g., phosphorylation or glycosylation). Polypeptides that can be used as NTR agonists typically are between 3 and 30 amino acids in length (e.g., 3, 4, 5, 6, 7, 8, 9, 10, 11, 12, 13, 14, 15, 20, 25, or 30 amino acids in length). For example, a polypeptide can be between 3 and 13 amino acids in length.

The term "amino acid" refers to natural amino acids, unnatural amino acids, and amino acid analogs, all in their D and L stereoisomers if their structures so allow. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Unnatural amino acids include, without limitation, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethyl glycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, pipecolic acid, N-methylarginine, 3,1-naphthylalanine, 3,2-naphthylalanine, and neo-tryptophan.

An "analog" is a chemical compound that is structurally similar to another but differs slightly in composition, as in the replacement of one atom by an atom of a different element, the presence of a particular functional group, or the replacement of an amino acid with another amino acid. An "amino acid analog" therefore is structurally similar to a naturally occurring amino acid molecule as is typically found in native polypeptides, but differs in composition such that either the C-terminal carboxy group, the N-terminal amino group, or the side-chain functional group has been chemically modified to another functional group. Amino acid analogs include, without limitation, natural and unnatural amino acids that are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide, and S-(carboxymethyl)-cysteine sulfone. Amino acid analogs may be naturally occurring, or can be synthetically prepared. Non-limiting examples of amino acid analogs include, without limitation, aspartic acid-(beta-methyl ester), an analog of aspartic acid; N-ethylglycine, an analog of glycine; and alanine carboxamide, an analog of alanine. Other examples of amino acids and amino acids analogs are listed in Gross and Meienhofer, *The Peptides: Analysis, Synthesis, Biology*, Academic Press, Inc., New York (1983).

The stereochemistry of a polypeptide can be described in terms of the topochemical arrangement of the side chains of the amino acid residues about the polypeptide backbone, which is defined by the peptide bonds between the amino acid residues and the I-carbon atoms of the bonded residues. In addition, polypeptide backbones have distinct termini and thus direction. The majority of naturally occurring amino acids are L-amino acids. Naturally occurring polypeptides are largely comprised of L-amino acids. D-amino acids are the enantiomers of L-amino acids and can form "inverso" polypeptides (i.e., peptides corresponding to native peptides but made up of D-amino acids rather than L-amino acids).

Polypeptides can be modified for use in vivo by the addition, at the amino- or carboxy-terminal end, of a stabilizing agent to facilitate survival of the polypeptide in vivo. This can be useful in situations in which peptide termini tend to be degraded by proteases prior to cellular uptake. Such blocking agents can include, without limitation, additional related or unrelated amino acid sequences that can be attached to the amino- and/or carboxy-terminal residues of a polypeptide (e.g., an acetyl group attached to the N-terminal amino acid or an amide group attached to the C-terminal amino acid). Such attachment can be achieved either chemically, during the synthesis of the polypeptide, or by recombinant DNA technology using methods familiar to those of ordinary skill in the art. In some cases, blocking agents such as pyroglutamic acid or other molecules known in the art can be attached to the amino- and/or carboxy-terminal residues, or the amino group at the amino terminus or the carboxy group at the carboxy terminus can be replaced with a different moiety.

Polypeptides also can contain an amino acid tag. A "tag" is generally a short amino acid sequence that provides a ready means of detection or purification through interactions with an antibody against the tag or through other compounds or molecules that recognize the tag. For example, tags such as c-myc, hemagglutinin, polyhistidine, or Flag® can be used to aid purification and detection of a polypeptide. As an example, a polypeptide with a polyhistidine tag can be purified based on the affinity of histidine residues for nickel ions (e.g., on a Ni-NTA column), and can be detected in western blots by an antibody against polyhistidine (e.g., the Penta-His antibody; Qiagen, Valencia, Calif.). Tags can be inserted anywhere within a polypeptide sequence, including at the amino- or carboxy-terminus.

NTR agonists that can be used as described herein also can be peptidomimetic compounds designed on the basis of the amino acid sequences of NT polypeptides. Peptidomimetic compounds are synthetic, non-peptide compounds having a three-dimensional conformation (i.e., a "peptide motif") that is substantially the same as the three-dimensional conformation of a selected polypeptide, and thus can confer the same or similar function as the selected polypeptide. Peptidomimetic compounds can be designed to mimic any of the NT polypeptides provided herein.

In some cases, a peptidomimetic compound can be protease resistant. Furthermore, peptidomimetic compounds may have additional characteristics that enhance therapeutic effects, such as increased cell permeability and prolonged biological half-life. Such compounds typically have a backbone that is partially or completely non-peptide, but with side groups that are identical or similar to the side groups of the amino acid residues that occur in the polypeptide upon which the peptidomimetic compound is based. Several types of chemical bonds (e.g., ester, thioester, thioamide, retroamide, reduced carbonyl, dimethylene and ketomethylene) can be used as substitutes for peptide bonds in the construction of peptidomimetic compounds.

Polypeptides that can be used as described herein can be produced by a number of methods, many of which are well known in the art. By way of example and not limitation, a polypeptide can be obtained by extraction from a natural source (e.g., from isolated cells, tissues, or bodily fluids), by expression of a recombinant nucleic acid encoding the polypeptide (as, for example, described herein), or by chemical synthesis (e.g., by solid-phase synthesis or other methods well known in the art, including synthesis with an ABI peptide synthesizer; Applied Biosystems, Foster City, Calif.).

NT analogs such as NT69L can be synthesized using Fmoc chemistry with t-butyl-protected side chains on an automated peptide synthesizer, for example. See, U.S. Pat. No. 6,214,790 and Cusack et al. (2000) Brain Res. 856:48-54. NT69L has the amino acid sequence N-methyl-Arg-Lys-Pro-L-neo-Trp-tert-Leu-Leu (SEQ ID NO:3). The L-neo-Trp residue can be synthesized by, for example, the method of Fauq et al. (Fauq et al. supra), or by methods disclosed in U.S. Pat. No. 6,214,790. Once synthesized, the polypeptide can be purified by, for example, HPLC (e.g., reverse phase HPLC).

NT polypeptides also can be prepared by recombinant technology using isolated nucleic acid molecules encoding the polypeptides. As used herein, "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand).

Nucleic acids encoding NT polypeptides can be contained within nucleic acid vectors. A vector is a replicon, such as a plasmid, phage, or cosmid, into which another nucleic acid segment may be inserted so as to bring about the replication of the inserted segment. Vectors that are useful to produce NT polypeptides typically are expression vectors, in which the nucleotides encode an NT polypeptide with an initiator methionine, operably linked to expression control sequences. As used herein, "operably linked" means incorporated into a genetic construct so that expression control sequences effectively control expression of a coding sequence of interest. An "expression control sequence" is a nucleic acid sequence that controls and/or regulates the transcription and translation of another nucleic acid sequence, and an "expression vector" is a vector that includes expression control sequences, so that a relevant nucleic acid segment incorporated into the vector is transcribed and translated. A coding sequence is "operably linked" and "under the control" of transcriptional and translational control sequences in a cell when a polymerase transcribes the coding sequence into mRNA, which then is translated into the polypeptide encoded by the coding sequence.

Methods well known to those skilled in the art may be used to subclone isolated nucleic acid molecules encoding NT polypeptides into expression vectors containing relevant coding sequences and appropriate transcriptional/translational control signals. See, for example, Sambrook et al., *Molecular Cloning: A Laboratory Manual* (2nd edition), Cold Spring Harbor Laboratory, New York (1989); and Ausuble et al., *Current Protocols in Molecular Biology*, Green Publishing Associates and Wiley Interscience, New York (1989). Expression vectors can be used to produce NT polypeptides in a variety of systems (e.g., bacteria, yeast, insect cells, and mammalian cells). Examples of suitable expression vectors include, without limitation, plasmids and viral vectors derived from herpes viruses, retroviruses, vaccinia viruses, adenoviruses, and adeno-associated viruses. A wide variety of expression vectors and systems are commercially available, including the pET series of bacterial expression vectors (Novagen, Madison, Wis.), the Adeno-X expression system (Clontech), the Baculogold baculovirus expression system (BD Biosciences Pharmingen, San Diego, Calif.), and the pCMV-Tag vectors (Stratagene, La Jolla, Calif.).

Expression systems that can be used for small or large scale production of NT polypeptides include, without limitation, microorganisms such as bacteria (e.g., *E. coli* and *B. subtilis*) transformed with recombinant bacteriophage DNA, plasmid DNA, or cosmid DNA expression vectors containing nucleic acid molecules encoding NT polypeptides; yeast (e.g., *S. cerevisiae*) transformed with recombinant yeast expression vectors containing nucleic acid molecules encoding NT polypeptides; insect cell systems infected with recombinant virus expression vectors (e.g., baculovirus) containing nucleic acid molecules encoding NT polypeptides; plant cell systems infected with recombinant virus expression vectors (e.g., tobacco mosaic virus) or transformed with recombinant plasmid expression vectors (e.g., Ti plasmid) containing nucleic acid molecules encoding NT polypeptides; or mammalian cell systems (e.g., primary cells or immortalized cell lines such as COS cells, CHO cells, HeLa cells, HEK 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with nucleic acid molecules encoding NT polypeptides.

NT polypeptides can be substantially pure NT polypeptides. The term "substantially pure" as used herein with reference to a polypeptide means the polypeptide is substantially separated from other molecules and compounds. Thus, a naturally occurring polypeptide that is substantially pure is substantially free of other polypeptides, lipids, carbohydrates, and nucleic acid with which it associates in nature. A non-naturally occurring polypeptide (e.g., a synthetic polypeptide or a peptidomimetic) that is substantially pure is substantially free of the chemical components included in the synthesis reaction. Typically, a substantially pure polypeptide will yield a single major band on a non-reducing polyacrylamide gel. A substantially pure NT polypeptide can be at least about 60 percent pure (e.g., at least about 65, 70, 75, 80, 85, 90, 95, or 99 percent pure). It is understood that an NT polypeptide is considered substantially pure if it has been purified and then mixed with, for example, an opioid receptor agonist (e.g., morphine), an adjuvant, or a pharmaceutical carrier, as the NT polypeptide is separated from the cellular components with which it is associated in nature or separated from the components with which it is associated in a synthesis reaction. Suitable methods for purifying NT polypeptides can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

Small molecules also can be used in the methods provided herein to treat pain. Such small molecules (i.e., non-polypeptide NTR agonists) can be isolated and identified using assays such as ELISA and binding assays (e.g., affinity chromatography). For example, NTR molecules can be coated in the wells of a microtiter plate or coupled to a chromatography resin. Cellular extracts or solutions containing a cocktail of small molecules can be incubated in the wells or with the resin. Molecules that do not bind can be washed away, while bound molecules can be eluted by, for example, washing with a buffer containing a relatively high concentration of salt.

Compositions

NTR agonists and opioid receptor agonists can be incorporated into compositions that can be used to treat pain. Any method for formulating and subsequently administering such compositions can be used. Dosing generally is dependent on the severity and location of the pain, with the course of treatment lasting from several days to several months, or until the underlying source of the pain (e.g., wound or disease) is alleviated or removed. Optimum dosages can vary depending on the relative potency of individual NTR agonists and opioid receptor agonists, and generally can be estimated based on $EC_{50}$ found to be effective in in vitro and in vivo animal models. Typically, dosage is from 0.01 μg to 100 g per kg of body weight. Compositions containing NTR agonists and opioid receptor agonists can be given once or more daily, weekly, or even less often.

The methods provided herein include the administration of pharmaceutical compositions and formulations that include an NTR agonist and an opioid receptor agonist. A composition containing at least one NTR agonist and at least one opioid receptor agonist can be admixed, encapsulated, conjugated or otherwise associated with other molecules, molecular structures, or mixtures of molecules such as, for example, liposomes, receptor targeted molecules, or oral, rectal, topical or other formulations, for assisting in uptake, distribution and/or absorption.

A "pharmaceutically acceptable carrier" is a pharmaceutically acceptable solvent, suspending agent, or any other pharmacologically inert vehicle for delivering one or more therapeutic compounds (e.g., NT69L and morphine) to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, by way of example and not limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions can be administered by a number of methods. Administration can be, for example, topical (e.g., transdermal, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). For treating tissues in the central nervous system, an NTR agonist and an opioid receptor agonist can be administered by injection or infusion into the cerebrospinal fluid, preferably with one or more agents capable of promoting penetration of the agonists across the blood-brain barrier.

Formulations for topical administration of NTR agonists and opioid receptor agonists include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be necessary or desirable.

Compositions and formulations for oral administration of NTR agonists and opioid receptor agonists include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Liposomes are vesicles that have a membrane formed from a lipophilic material and an aqueous interior that can contain a composition provided herein. Liposomes can be particularly useful due to their specificity and the duration of action they offer from the standpoint of drug delivery. Liposome compositions can be formed from phosphatidylcholine, dimyristoyl phosphatidylcholine, dipalmitoyl phosphatidylcholine, dimyristoyl phosphatidylglycerol, or dioleoyl phosphatidylethanolamine, for example. Numerous lipophilic agents are commercially available, including Lipofectin® (Invitrogen/Life Technologies, Carlsbad, Calif.) and Effectene3 (Qiagen, Valencia, Calif.).

Compositions containing an NTR agonist and an opioid receptor agonist can further encompass any pharmaceutically acceptable salts, esters, or salts of such esters, or any other compound which, upon administration to a mammal (e.g., a human), is capable of directly or indirectly providing the biologically active agonist or residue thereof. Accordingly, for example, pharmaceutically acceptable salts of an NTR agonist or an opioid receptor agonist, prodrugs of an NTR agonist or an opioid receptor agonist, pharmaceutically acceptable salts of such prodrugs, and other bioequivalents can be used as described herein. A prodrug is a therapeutic agent that is prepared in an inactive form and is converted to an active form (i.e., drug) within the body or cells thereof by the action of endogenous enzymes or other chemicals and/or conditions. A pharmaceutically acceptable salt of an NTR agonist or an opioid receptor agonist can be a salt that retains the desired biological activity of the parent agonist molecule without imparting undesired toxicological effects. Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed from elemental anions (e.g., chlorine, bromine, and iodine).

Pharmaceutical compositions containing an NTR agonist and an opioid receptor agonist also can incorporate penetration enhancers that promote the efficient delivery of, for example, polypeptides, small molecules, or other molecules, to the skin of animals. Penetration enhancers can enhance the diffusion of both lipophilic and non-lipophilic drugs across cell membranes. Penetration enhancers can be classified as belonging to one of five broad categories, i.e., surfactants (e.g., sodium lauryl sulfate, polyoxyethylene-9-lauryl ether and polyoxyethylene-20-cetyl ether); fatty acids (e.g., oleic acid, lauric acid, myristic acid, palmitic acid, and stearic acid); bile salts (e.g., cholic acid, dehydrocholic acid, and deoxycholic acid); chelating agents (e.g., disodium ethylenediaminetetraacetate, citric acid, and salicylates); and non-chelating non-surfactants (e.g., unsaturated cyclic ureas).

Compositions provided herein can contain other adjunct components conventionally found in pharmaceutical compositions. Thus, the compositions provided herein can include compatible, pharmaceutically active materials such as, for example, antipruritics, astringents, local anesthetics, or anti-inflammatory agents, or additional materials useful in physically formulating various dosage forms such as dyes, flavoring agents, preservatives, antioxidants, opacifiers, thickening agents, or stabilizers. Furthermore, a composition provided herein can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the NTR agonists or opioid receptor agonists within the compositions. The formulations can be mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the agonists of the formulation.

Pharmaceutical formulations can be presented conveniently in unit dosage form, and can be prepared according to conventional techniques well known in the pharmaceutical industry. Such techniques include the step of bringing into association the active ingredients (e.g., NT69L and morphine) with the desired pharmaceutical carrier(s). Typically, a formulation can be prepared by uniformly bringing the active ingredients into intimate association with liquid carriers or finely divided solid carriers or both, and then, if necessary, shaping the product. Formulations can be sterilized if desired, provided that the method of sterilization does not interfere with the effectiveness of the agonists contained in the formulation.

Compositions containing an NTR agonist and an opioid receptor agonist can be formulated into any of many possible dosage forms such as, but not limited to, tablets, capsules, liquid syrups, soft gels, suppositories, and enemas. Compositions also can be formulated as suspensions in aqueous, non-aqueous or mixed media. Aqueous suspensions further can contain substances that increase the viscosity of the suspension including, for example, sodium carboxymethylcellulose, sorbitol, and/or dextran. Suspensions also can contain stabilizers.

The synergistic combination can be delivered transdermally, by means of a transdermal patch for systemic effect, orally or as an intranasal spray for systemic effect, as a suppository, intravenously, intramuscularly or subcutaneously, or as a topical application (cream or patch), etc. When administered orally, in a "sustained release" formulation, the NTR agonist can be on the outside and the opioid receptor agonist (e.g., an opiate) on the inside. This can allow the NTR agonist to be released first, and the opioid receptor agonist later. The dopaminergic blockade caused by the NTR agonist can therefore diminish or eliminate the reward system and so addictive behaviour. The reverse formulation, with the opioid receptor agonist on the outside, however, can prevent a polypeptide NTR agonist peptide from degradation by gut peptidases.

The invention will be further described in the following examples, which do not limit the scope of the invention described in the claims.

EXAMPLES

Examples of neurotensin analogs and neurotensin receptor agonists, each with neotryptophan, include those listed in the following tables. The table immediately below lists neurotensin analogs that include neo-tryptophan.

| | |
|---|---|
| NT64L [L-neo-Trp$^{11}$]NT(8-13) | (SEQ ID NO. 14) |
| NT64D [D-neo-Trp$^{11}$]NT(8-13) | (SEQ ID NO. 13) |
| NT65L [L-neo-Trp$^{11}$, tert-Leu$^{12}$]NT(8-13) | (SEQ ID NO. 15) |
| NT65D [D-neo-Trp$^{11}$, tert-Leu$^{12}$]NT(8-13) | (SEQ ID NO. 28) |
| NT66L [D-Lys$^{8}$, L-neo-Trp$^{11}$, tert-Leu$^{12}$]NT(8-13) | (SEQ ID NO. 17) |
| NT66D [D-Lys$^{8}$, D-neo-Trp$^{11}$, tert-Leu$^{12}$]NT(8-13) | (SEQ ID NO. 16) |
| NT67L [D-Lys$^{8}$, L-neo-Trp$^{11}$]NT(8-13) | (SEQ ID NO. 18) |
| NT67D [D-Lys$^{8}$, D-neo-Trp$^{11}$]NT(8-13) | (SEQ ID NO. 29) |

-continued

| | |
|---|---|
| NT69L [N-methyl-Arg$^{8}$,L-Lys$^{9}$,L-neo-Trp$^{11}$, tert-Leu$^{12}$]NT(8-13) | (SEQ ID NO. 19) |
| NT69D [N-methyl-Arg$^{8}$,L-Lys$^{9}$,D-neo-Trp$^{11}$, tert-Leu$^{12}$]NT(8-13) | (SEQ ID NO. 30) |
| NT71L [N-methyl-Arg$^{8}$,DAB$^{9}$,L-neo-Trp$^{11}$, tert-leu$^{12}$]NT(8-13) | (SEQ ID NO. 21) |
| NT71D [N-methyl-Arg$^{8}$,DAB$^{9}$,D-neo-Trp$^{11}$, tert-leu$^{12}$]NT(8-13) | (SEQ ID NO. 31) |
| NT72L [D-Lys$^{9}$,L-neo-Trp$^{11}$,tert-Leu$^{12}$]NT(9-13) | (SEQ ID NO. 22) |
| NT72D [D-Lys$^{9}$,D-neo-Trp$^{11}$,tert-Leu$^{12}$]NT(9-13) | (SEQ ID NO. 32) |
| NT73L [D-Lys$^{9}$,L-neo-Trp$^{11}$]NT(9-13) | (SEQ ID NO. 23) |
| NT73D [D-Lys$^{9}$,D-neo-Trp$^{11}$]NT(9-13) | (SEQ ID NO. 33) |
| NT74L [DAB$^{9}$,L-neo-Trp$^{11}$,tert-Leu$^{12}$]NT(9-13) | (SEQ ID NO. 24) |
| NT74D [DAB$^{9}$,Pro,D-neo-Trp$^{11}$,tert-Leu$^{12}$]NT(9-13) | (SEQ ID NO. 34) |
| NT75L [DAB$^{8}$,L-neo-Trp$^{11}$]NT(8-13) | (SEQ ID NO. 25) |
| NT75D [DAB$^{8}$,D-neo-Trp$^{11}$]NT(8-13) | (SEQ ID NO. 35) |
| NT76L [D-Orn$^{9}$,L-neo-Trp$^{11}$]NT(8-13) | (SEQ ID NO. 26) |
| NT76D [D-Orn$^{9}$,D-neo-Trp$^{11}$]NT(8-13) | (SEQ ID NO. 36) |
| NT77L [D-Orn$^{9}$,L-neo-Trp$^{11}$,tert-Leu$^{12}$]NT(8-13) | (SEQ ID NO. 27) |
| NT77D [D-Orn$^{9}$,D-neo-Trp$^{11}$,tert-Leu$^{12}$]NT(8-13) | (SEQ ID NO. 37) |
| NT78L [N-methyl-,D-Orn$^{9}$,L-neo-Trp$^{11}$, tert-Leu$^{12}$]NT(8-13) | (SEQ ID NO. 38) |
| NT78D [N-methyl-Arg$^{8}$,D-Orn$^{9}$,D-neo-Trp$^{11}$, tert-Leu$^{12}$]NT(8-13) | (SEQ ID NO. 39) |

TABLE I

Amino Acid Sequence and Analytical Data for NT, NT[8-13], and KK1-19

| pep- | amino acid sequence | | | | | | | | | | | | MW (g/mol) |
|---|---|---|---|---|---|---|---|---|---|---|---|---|---|
| tide | 1 | 2 | 3 | 4 | 5 | 6 | 7 | 8 | 9 | 10 | 11 | 12 | 13 | obsd$^{1}$(calcd)$^{h}$ |
| NT | Glu | L-Leu | L-Tyr | L-Glu | L-Asn | L-Lys | L-Pro | L-Arg | L-Arg | L-Pro | L-Tyr | L-Ile | L-Leu | NA' |
| NT [8-13] | — | — | — | — | — | — | — | L-Arg | L-Arg | L-Pro | L-Tyr | L-Ile | L-Leu | NA |
| KK1 | — | — | — | — | — | — | — | $N_2$-L-Hlys | L-Arg | L-Pro | L-Tyr | L-Ile | L-Leu | 829.5 (829.0) |
| KK2 | — | — | — | — | — | — | — | $N_3$-1$^{d}$ | L-Arg | L-Pro | L-Tyr | L-Ile | L-Leu | 843.5 (843.0) |
| KK3 | — | — | — | — | — | — | — | $N_3$ 2 | L-Arg | L-Pro | L-Tyr | L-Ile | L-Leu | 857.5 (857.1) |
| KK4 | — | — | — | — | — | — | — | $N_3$-3 | L-Arg | L-Pro | L-Tyr | L-Ile | L-Leu | 871.5 (872.1) |
| KK5 | — | — | — | — | | — | — | $N_3$-L-Lys | L-Arg | L-Pro | L-Tyr | L-Ile | L-Leu | 815.5 (815.0) |
| KK6 | — | — | — | — | — | — | — | $N_3$-4 | L-Arg | L-Pro | L-Tyr | L-Ile | L-Leu | 829.6 (829.0) |
| KK7 | — | — | — | — | — | — | — | $N_3$-5 | L-Arg | L-Pro | L-Tyr | L-Ile | L-Leu | 843.5 (843.0) |
| KK8 | — | — | — | — | — | — | — | $N_3$-6 | L-Arg | L-Pro | L-Tyr | L-Ile | L-Leu | 857.6 (858.1) |
| KK9 | — | — | — | — | — | — | — | $N_3$-L-Orn | L-Arg | L-Pro | L-Tyr | L-Ile | L-Leu | 801.4 (801.0) |
| KK10 | — | | — | — | — | | — | $N_3$-7 | L-Arg | L-Pro | L-Tyr | L-Ile | L-Leu | 815.5 (815.0) |
| KK11 | — | | — | — | — | — | — | $N_3$-8 | L-Arg | L-Pro | L-Tyr | L-Ile | L-Leu | 829.5 (829.0) |
| KK12 | | | | | | | | $N_3$-9 | L-Arg | L-Pro | L-Tyr | L-Ile | L-Leu | 843.5 (814.0) |
| KK13 | | | | | — | | | $N_3$ L-Hlys | L-Arg | L-Pro | L-Tyr | L-tert-Leu | L-Leu | 829.5 (829.0) |
| KK14 | | | — | — | | | — | $N_3$-L-Hlys | L-Arg | L-Pro | L-Trp | L tert Leu | L-Leu | 852.5 (852.0) |
| KK15 | | — | — | — | — | — | — | $N_3$-L-Arg | L-Arg | L-Pro | L-Tyr | L-Ile | L-Leu | 843.5 (843.0) |
| KK16 | | | | — | | — | | 10 | L-Arg | L-Pro | L-Tyr | L-Ile | L-Leu | 831.6 (831.0) |

TABLE I-continued

| Amino Acid Sequence and Analytical Data for NT, NT[8-13], and KK1-19 | | | | | | | | | | | | | | |
|---|---|---|---|---|---|---|---|---|---|---|---|---|---|---|
| pep- | amino acid sequence | | | | | | | | | | | | | MW (g/mol) |
| tide | 1 | 2 | 3 | 4 | 5 | 6 | 7 | 8 | 9 | 10 | 11 | 12 | 13 | obsd[1](calcd)[h] |
| KK17 | | | — | — | | | | 11 | L-Arg | L-Pro | L-Tyr | L-Ile | L-Leu | 845.6 (845.0) |
| KK18 | | | | | — | — | — | 12 | L-Arg | L-Pro | L-Tyr | L-Ile | L-Leu | 843.6 (843.0) |
| KK19 | | — | — | — | — | — | | 13 | L-Arg | L-Pro | L-Tyr | L-Ile | L-Leu | 843.6 (843.0) |

See Kokko, J. Med. Chem., (2003) 46: 4141-4148, incorporated herein by reference.

Example 1

Treating Pain Using a Combination of an NTR Agonist (NT69L) and an Opioid Receptor Agonist Sprague Dawley male rats (150-250 g) were housed in a temperature controlled room with a 12:12 hour light/dark cycle and were given standard rat chow and water ad lib. Animals were injected with either NT69L or morphine or the combination of the two drugs in separate injections, one immediately after the other. All drugs were injected intraperitoneally. Fifteen minutes after the injection, animals were tested on the hot plate (time=0 on the graph of FIG. 1). The baseline hot plate data were obtained immediately prior to the experiment. The hot plate methods are described elsewhere (Tyler et al., *Brain Research,* 792:246-52 (1998)). Briefly, the hot plate was performed to determine pain sensitivity. The rats were placed on a metal plate (15×20 cm), maintained at a temperature of 52.5±0.15° C. The latency between the time the rat is placed on the surface and the time it licks either of its hind paws was measured. Failure to respond in 30 sec resulted in ending the trial and assignment of that latency. Hot plate tests were scored as the percent of Maximum Possible Effect (% MPE) and calculated according to the following equation: % MPE=[(post-drug latency−pre-drug latency)/(cut-off−pre-drug latency)]×100; where 30 second is the cut-off.

Animals treated with both NT69L and morphine exhibited an antinociceptive effect that was greater than the sum of the effects of each compound separately (FIG. 1). These results indicate that the combination of an NTR agonist and an opioid receptor agonist provide a level of pain relief that is greater than that observed with either an NTR agonist or an opioid receptor agonist alone.

Example 2

Treating Pain Using a Combination of an NTR Agonist (NT72 or NT77) and an Opioid Receptor Agonist As in Example 1, Sprague Dawley male rats (150-250 g) were housed in a temperature controlled room with a 12:12 hour light/dark cycle and were given standard rat chow and water ad lib. Animals were injected with either NT77, NT72, morphine, or the combination of morphine with either NT77 or NT72 in separate injections, one immediately after the other. All drugs were injected intraperitoneally. Fifteen minutes after the injection, animals were tested on the hot plate (time=0 on the graph of FIG. 2). The baseline hot plate data were obtained immediately prior to the experiment. The hot plate methods are described elsewhere (Tyler et al., *Brain Research,* 792:246-52 (1998)). Briefly, the hot plate was performed to determine pain sensitivity. The rats were placed on a metal plate (15×20 cm), maintained at a temperature of 52.5±0.15° C. The latency between the time the rat is placed on the surface and the time it licks either of its hind paws was measured. Failure to respond in 30 sec resulted in ending the trial and assignment of that latency. Hot plate tests were scored as the percent of Maximum Possible Effect (% MPE) and calculated according to the following equation: % MPE=[(post-drug latency−pre-drug latency)/(cut-off−pre-drug latency)]×100; where 30 second is the cut-off.

Figure 2:
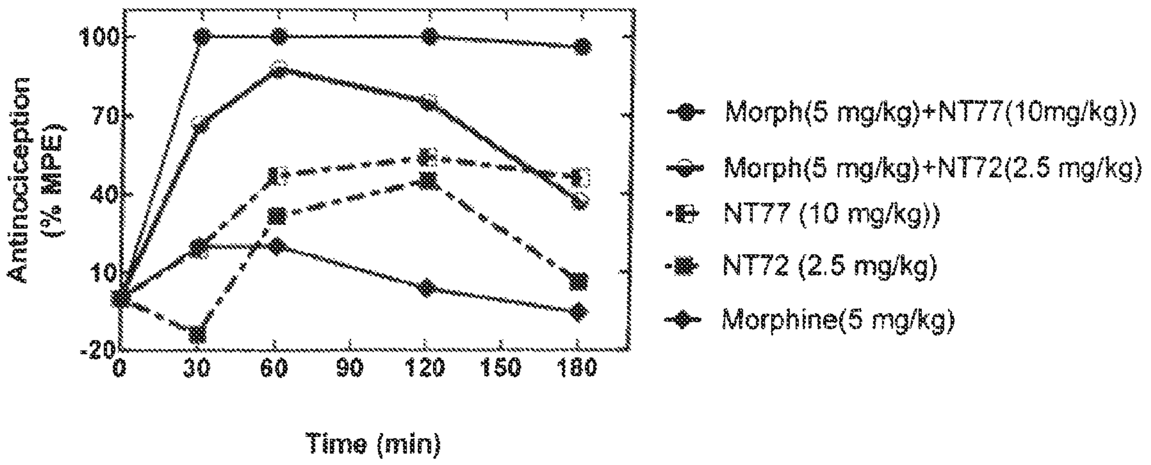
FIG. 2 is a graph plotting the percent maximum possible effect at the indicated time post injection for rats treated with morphine alone (5.0 mg/kg), NT77 alone (10.0 mg/kg), NT72 alone (2.5 mg/kg), both morphine (5.0 mg/kg) and NT77 (10.0 mg/kg), or both morphine (5.0 mg/kg) and NT72 (2.5 mg/kg).

Animals treated with both NT77 and morphine or NT72 and morphine exhibited an antinociceptive effect that was greater than the sum of the effects of each compound separately (FIG. 2). These results indicate that the combination of an NTR agonist and an opioid receptor agonist provide a level of pain relief that is greater than that observed with either an NTR agonist or an opioid receptor agonist alone.

Example 3

Male CD-1 mice (25-30 g) are used in each example. Drugs are administered systemically via subcutaneous or intraperitoneal injections. Gastrointestinal transit is assessed by measuring the distance traveled by a charcoal meal (Paul and Pasternak 1988), incorporated herein by reference.

Analgesia is assessed 30 minutes post-injection using the radiant heat tail-flick assay. Baseline latencies range between 2.0 and 3.2 seconds. A maximal cutoff latency of 10 seconds is set to minimize tissue damage. Analgesia is assessed quantally as a doubling or greater of the baseline latency for each mouse. Quantal measures have long been used in this assay (D'Amour and Smith, 1941; Le Bars et al., 2001), as previously published by Pasternak et al, 19801a,b; Rossi et al, 1995, 1996; Neilan et al., 2001). Groups of mice are compared using Fisher's extract test. ED50 values and 95% confidence limits are calculated by probit analysis (Tallarida, 2000).

To assess the statistical significance of the combinations, complete dose-response data are determined for each compound and are examined with probit regression analysis with the aid of Pharm tools Pro (McCary Group, Elkins Park, Pa.). Each opiate compound is paired in a fixed-ratio combination with the neurotensin in question (NT69L or other) to assess whether the combination displays enhanced potency versus opiate alone indicative of synergism. That assessment is made by determining the composite line of additivity for the combination and comparing that line to the dose-response regression line of the experimentally determined combination using ANOVA (Tallarida, 2000). A graphical assessment of synergy is also presented using isobolographic analysis (Roerig et al., 1984; Kolesnikov et al., 1996, 2000; Tallarida and Raffa, 1996; Tallarida et al., 1997).

Although the foregoing invention has, for the purposes of clarity and understanding, been described in some detail by way of illustration and example, it will be obvious that certain changes and modifications may be practiced which will still fall within the scope of the appended claims. It will also be understood that any feature or features from any one embodiment, or any reference cited herein, may be used with any combination of features from any other embodiment.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It is to be understood that any feature or aspect of any composition, formulation, combination, or method described herein can be used together with any other composition, formulation, combination, or method described herein.

What is claimed is:

1. A method for treating pain, said method comprising administering a neurotensin receptor agonist and morphine to a mammal in need thereof, wherein the neurotensin receptor agonist is selected from the group consisting of NT(1-13) (SEQ ID NO. 4), NT(8-13) (SEQ ID NO. 5), NT69L (SEQ ID NO. 19), NT69L' (SEQ ID NO. 20), and NT76 (SEQ ID NO. 26).

2. The method of claim 1, wherein said neurotensin receptor agonist is a polypeptide.

3. The method of claim 2, wherein said polypeptide comprises an amino acid analog.

4. The method of claim 3, wherein said amino acid analog is L-neo-Trp.

5. The method of claim 1, wherein said administering is by injection.

6. The method of claim 1, wherein said mammal is a human.

7. The method of claim 1, wherein said morphine is administered prior to administering said neurotensin receptor agonist.

8. The method of claim 1, wherein said neurotensin receptor agonist is administered prior to administering said morphine.

9. The method of claim 1, wherein said neurotensin receptor agonist and said morphine is administered as a single composition.

10. The method of claim 1, wherein said method comprises administering two or more neurotensin receptor agonists.

* * * * *